US006112749A

United States Patent [19]

Hall et al.

[11] Patent Number: 6,112,749

[45] Date of Patent: Sep. 5, 2000

[54] FLAVOR DOT ODORIZER AND METHOD

[75] Inventors: Warren Grimes Hall; David Charles Rubin, both of Durham, N.C.

[73] Assignee: Appetek, Inc., Durham, N.C.

[21] Appl. No.: 09/014,429

[22] Filed: Jan. 27, 1998

[51] Int. Cl.[7] ...................................................... A61B 19/00

[52] U.S. Cl. ........................... 128/898; 604/77; 606/236; 215/11.1

[58] Field of Search ............................... 604/77, 78, 500; 606/236; 215/11.1 R, 11.1, 386, 227, 230, DIG. 3, DIG. 7; 222/133, 145, 158; 128/898

[56] References Cited

U.S. PATENT DOCUMENTS

| | | | |
|---|---|---|---|
| 3,266,910 | 8/1966 | Barnby . | |
| 3,682,344 | 8/1972 | Lopez . | |
| 3,957,966 | 5/1976 | Valan . | |
| 4,071,614 | 1/1978 | Grimm, III . | |
| 4,192,307 | 3/1980 | Baer . | |
| 4,296,139 | 10/1981 | Khan et al. . | |
| 4,521,427 | 6/1985 | Nietupski | 514/354 |
| 4,582,492 | 4/1986 | Etter et al. | 434/236 |
| 4,983,394 | 1/1991 | Hussein et al. . | |
| 5,013,557 | 5/1991 | Tai . | |
| 5,013,716 | 5/1991 | Cherukuri et al. . | |
| 5,078,733 | 1/1992 | Eveleigh et al. | 606/236 |
| 5,244,122 | 9/1993 | Botts . | |
| 5,542,922 | 8/1996 | Petterson et al. . | |

OTHER PUBLICATIONS

Alberts, J.R., (1984). "Sensory–perceptual development in the Norway rat: A view toward comparative studies." In R. Kail & N.E. Spear (Eds.), *Comparative Perspectives on the Development of Memory* pp. 65–101.

Benson, J.D. & Masor, M.L. (1994). "Infant formula development: Past, present and future." *Endorcrine Regulations*, 28, 9–16.

Blass, E.M. (1990). "Suckling: Determinants, changes, mechanisms, and lasting impressions," *Developmental Psychology*, 26, pp. 520–.

Blass, E.M.; Ganchrow, J.R.; and Steiner, J.E. (1984). "Classical conditioning in newborn humans 2–48 hours of age." *Infant Behavior and Development*, 7, 223–235.

Desor, J.A. (1973) "Taste in acceptance of sugars by human infants." *Journal of Comparative and Physiological Psychology*, 84, pp. 496–501.

Engen, T.; Lipsitt, L.P.; & Kaye, H. (1963). "Olfactory responses and adaptation in the human neonate." *Journal of Comparative and Physiological Psychology*, 56, pp. 73–77.

Hall, W.G. & Oppenheim, R.W. "Developmental psychobiology: Prenatal, perinatal, and early postnatal aspects of behavioral development." *Ann. Rev. Psychol.*, 1987, 38, pp. 91–128.

Hauser, H., et al. (1993). "A comparative Evaluation of whey hydrolysate and whey–predominant formulas: How well do infants accept and tolerate them?" *Clinical Pediatrics*, xx, pp. 433–437.

Johanson, I.B. & Hall, W.G. (1979). "Appetitive learning in 1–day–old rat pups." *Science*, 205, pp. 419–421.

Johanson, I.B. & Hall, W.G. (1980). "The ontogeny of feeding in rats: III. Thermal determinants of early ingestive responding." *J. Comp. Physiol. Psychol.*, 94, pp. 977–992.

(List continued on next page.)

*Primary Examiner*—Corrine McDermott
*Attorney, Agent, or Firm*—Rick Martin; Patent Law Offices of Rick Martin, P.C.

[57] ABSTRACT

A method and apparatus is taught to help infants change diets. An absorbent pad having an odorant is placed on a baby bottle so as to be near the baby's nose when ingesting. First the odorant is paired to a flavored diet of the baby. Then the odorant is coupled to a novel diet which the baby is not so fond of. The result is the baby ingests more than usual of the novel diet. Other aspects include a flavor ring on a baby bottle or a bowl and a plurality of flavor dots on a baby bottle or bowl. The inventive concept of placing a pleasing odorant near a user's nose during drinking can help babies, elderly people and even pets ingest more fluids.

22 Claims, 7 Drawing Sheets

OTHER PUBLICATIONS

Johanson, I.B. & Hall, W.G. (1982). "Appetitive conditioning in neonatal rats: Conditioned orientation to a novel odor." *Dev. Psychobiol.*, 15, pp. 379–397.

Johanson, I.B.; Hall, W.G.; & Polefron, J.M. (1984). "Appetitive conditioning in neonatal rats: Conditioned ingestive responding to stimuli paired with oral infusions of mild." *Dev. Psychobiol.*, 17, pp. 357–381.

Johanson, I.B. & Terry, L.M. (1984). "Learning in infancy: A mechanism for behavioral change during development." In E.M. Blass (Ed.), *Developmental psychobiology and behavioral ecology. Handbook of Behavioral Neurobiology*, vol. 9, pp. 245–281.

Kaye, H. (1967). "Infant sucking behavior and its modification." In L.P. Lippsitt & C.C. Spiker (Eds.), *Advances in Child Development and Behavior*. vol. 3 pp. 1–52.

Kron, R.E. (1968). "The effect of arousal and of learning upon sucking behavior in the newborn." Recent *Advances in Biological Psychiatry*, 10, pp. 302–313.

Kron, R.E. & Litt, M. (1971). "Fluid mechanics of nutritive sucking behavior: The suckling infant's oral apparatus analyzed as a hydraulic pump." *Medical & Biological Engineering*, 9, pp. 45–60.

Lipsitt, L.P.; Reilly, B.M.; Butcher, M.J.; & Greenwood, M.M. (1976). "The stability and interrelationships of newborn sucking and heart rate." *Developmental Psychobiology*, 9, pp. 305–310.

Makin, J.W. & Porter, R.H. (1989). "Attractiveness of lactating females' breast odors to neonates." *Child Development*, 60, pp. 803–810.

Medoff–Cooper, B.; Verklan, T.; & Carlson, S. (1993). "The development of sucking patterns and physiologic correlates in very–low–weight infants." *Nursing Research*, 42, pp. 100–105.

Mennella, J.A. (1995). "Mother's milk: A medium for early flavor experiences." *Journal of Human Lactation*, 11, pp. 39–45.

Mennella, J.A. & Beauchamp, G.K. (1994). "The infant's responses to flavored mild." *Infant Behavior and Development*, 17, pp. 819.

Nysenbaum, A.N. & Smart, J.L. (1982). "Sucking behavior and mild intake of neonates in realtion to milk fat content" *Early Human Development*, 6, pp. 205–213.

Porter, R.H.; Makin, J.W.; Davis, L.B.; & Christensen, K.M. (1991). "An assessment of the salient olfactory environment of formula–fed infants." *Physiology & Behavior*, 50, pp. 907–911.

Rosenblatt, J.S. (1971). "Sucking and home orientation in the kitten: A comparative developmental study." In E. Tobach, L.R. Arnonson & E. Shaw (eds.), The *Biopsychology of Development*, pp. 345–410.

Rozin, P. (1982). "Taste–smell confusions and the duality of the olfactory sense." *Perception & Psychophysics*, 31, 397–401.

Rubin, D.C. & Wenzel, A.E. (1996). "One hundred years of forgetting: A quantitative description of retention." *Psychological Review*, 103, pp. 734–760.

Sampson, H.A.; James, J.M.; & Bernhisel–Broadbent, J. (1992). "Safety of an amino acid–derived infant formula in children allergic to cow mild." *Pediatrics*, 90, pp. 463–465.

Santosham, M., et al. (1982). "Oral rehydration therapy of infantile diarrhea: A controlled study of well–nourished children hospitalized in the United States and Panama." *The New England Journal of Medicine*, 306, pp. 1070–1076.

Schaal, B. (1988). Review: "Olfaction in infants and children: developmental and functional perspectives." *Chemical Senses*, 13, pp. 145–190.

Schleidt, M. & Genzel, C. (1990). "The significance of mother's perfume for infants in the first weeks of their life." *Ethology & Sociobiology*, 11, pp. 145–154.

Spear, N.E. & Rudy, J.W. (1991). "Tests of the ontogeny of learning and memory: Issues, methods, and results." In H.N. Shair; G.A. Barr; & M.A. Hofer (Eds.), Developmental Psychobiology: *New Methods and Changing Concepts*, pp. 84–113.

Steiner, J.E. (1977). "Facial expressions of the neonate infant indicating the hedonics of food–related chemical stimult." In J.M. Weiffenbach (Ed.), *Taste and Development. The Genesis of Sweet Preference*, pp. 173–188.

Stickrod, G.; Kimble, D.P.; & Smotherman, W.P. (1982). "In utero taste/odor aversion conditioning in the rat." *Physiology & Behavior*, 28, pp. 5–7.

Sullivan, S.A. & Birch, L.L. (1994). "Infant dietary experience and acceptance of solid foods." *Pediatrics*, 93, pp. 271–277.

Sullivan, R.M.; Taborsky–Barba, S.; Mendoza, R.; Itano, A.; Leon, M.; Cotman, C.W.; Payne, T.F.; & Lott, I. (1991). "Olfactory classical conditioning in neonates." *Pediatrics*, 87, pp. 511–518.

Teicher, M.H. & Blass, E.M. (1977). "First suckling response of the newborn albino rat: The roles of olfaction and amniotic fluid." *Science*, 198, pp. 635–636.

Weingarten, H.P. (1984). "Meal initiation controlled by learned cues: Basic behavioral properties." *Appetite*, 5, pp. 147–158.

SCHEDULE OF EXPERIMENT

<table>
<tr><td>BASELINES (DAY1)</td><td>TRAINING (DAYS 1-3)</td><td>IMMEDIATE TESTS (DAY 4)</td><td>DELAYED TESTS (DAY 10)</td></tr>
<tr><td>SESSION 1</td><td>HOME TRAINING</td><td>SESSION 2</td><td>SESSION 3</td></tr>
<tr><td>TEST SOL | STD DIET |<br>STD DIET + FLAVOR-DOT A</td><td>STD DIET + FLAVOR-DOT A</td><td>TEST SOL +<br>FLAVOR-DOTS A, B, & C</td><td>TEST SOL +<br>FLAVOR-DOTS A, B, & C</td></tr>
</table>

NOTE: DURING TESTING, FLAVOR-DOT A CONTAINS THE SAME ODOR USED DURING TRAINING, FLAVOR-DOT B CONTAINS A NOVEL ODOR AND FLAVOR-DOT C IS UNSCENTED OR "BLANK")

FIG. 2

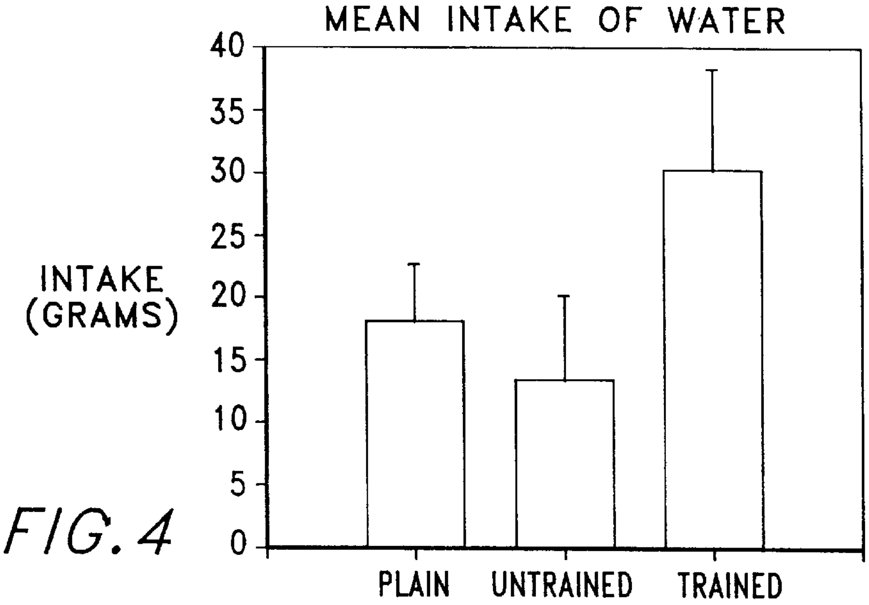
FIG. 4
INITIAL EXPOSURE
| | INTAKE(GRAMS) | SUCKS |
|---|---|---|
| FORMULA ALONE | 34 | 140 |
| FORMULA WITH DOT | 30 | 144 |
FIG. 5
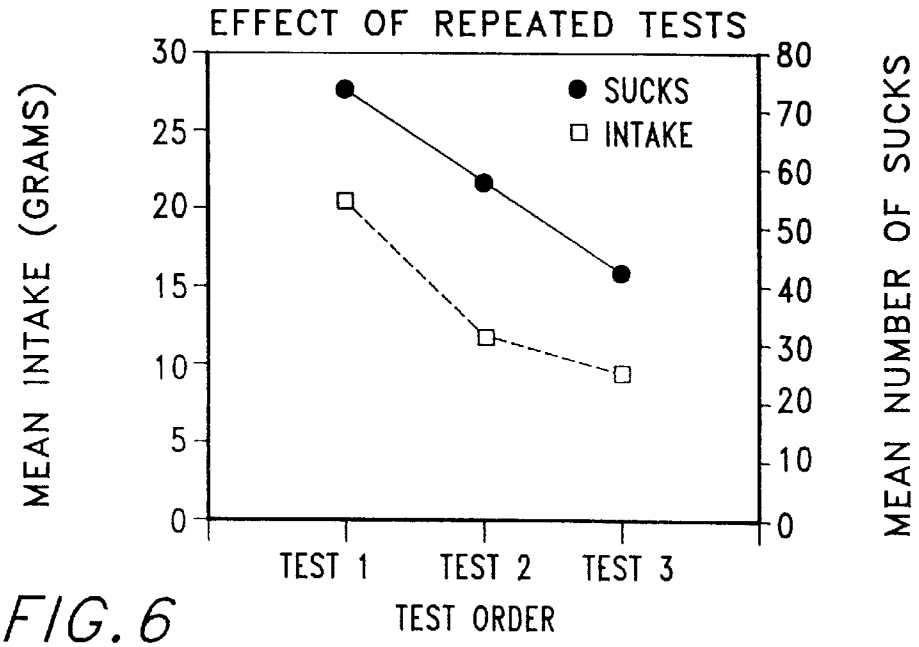
FIG. 6

FLAVOR DOT ODORIZER AND METHOD

FIELD OF INVENTION

The present invention relates to the placement of an absorptive material containing a chosen odorant on a baby bottle and the like in order to induce ingestion of the contents of the baby bottle via the conditioned luring effect of the odorant, wherein the luring effects were previously established by a classical conditioning process.

BACKGROUND OF THE INVENTION

Specific Aims

The Problem of Transitions Between Formulas for Infants. At one time or another, many infants experience feeding difficulties that can vary from mild fussiness to diet rejection. Typically, feeding disruptions last only for a few days and are of little consequence. But, for a number of infants who must, for one reason or another, make a transition between diets, from mothers' milk to formula, or from one formula to another, there can be more profound food rejection resulting from the diet transition. Such problems can be particularly severe in infants who must change to special diets that provide specific supplementation (Hoekelman et al., 1997). Such infants often resist pediatricians' and parents' attempts to introduce these therapeutic diets, apparently rejecting diets because they are novel or distasteful (e.g. Hauser et al., 1993). This unwillingness to consume the special formula can create distress and anxiety for parents and can result in a further deterioration of the infant's condition. Sometimes the problems can be so severe they require the use of intragastric or intravenous feeding and expensive hospital care.

Significance

The Diet Transition Problems of Infants. Infants are frequently required to switch from one diet to another. These transitions occur because of convenience, aesthetics, economics, or, in the most challenging situations when they are medically indicated. The transition can be from breast to bottle or from one bovine-based formula product to another. Sometimes it is from a standard formula to a specialized diet specifically formulated for a particular metabolic problem (Benson & Masor, 1994; Sampson, James, & Bernhisel-Broadbent, 1992). These diet transitions can be difficult for infants and the parents because infants may show mild to vigorous rejection of the new diet or feeding mode (Hauser et al., 1993). The present invention is oriented toward facilitating these diet transitions by improving the acceptance or preference for the new diet. This product should have a broad utility and be helpful even when only mild difficulties are to be expected. However, testing and product development is also oriented to situations where medical need dictates a diet transition and in which there is a recognized reluctance of infants to make a smooth diet transition.

The most common medical indication for a diet transition is a suspected allergy to proteins in bovine-based formulas (Host & Halken, 1990; Sampson, et al., 1992; Hoekelman et al., 1997). Formula companies market several soybean-based diets (our current market survey shows approximately 30% of formula offered on market shelves to be soy-based) to address this problem. They are not as sweet as cow or human milk, but the manufacturers have worked hard to make the taste and odor of these diets acceptable to infants (and their parents). There is usually resistance to this formula transition, though eventually babies will adjust to these soy diets and consume them.

To avoid allergic reactions, some babies need a predigested formula (Benson & Masor, 1994; e.g., Alimentum™, Nutramigen™, Pregestimil™) in which short peptides or amino acids replace the protein source. These diets taste bad to adults (and apparently to infants) and with these diets resistance to the diet transition can be much greater.

Finally, some babies are born with metabolic abnormalities, usually in the metabolism of a specific amino acid (e.g. homocystein, or phenylalanine, or valine). These infants need to be fed a formula that is specially constructed to deal with the problem (e.g. a phenylalanine free formula such as Lofenelac for phenylketonuria). These diets, apparently, are also very unpleasant to infants and can be difficult to get the infants to consume. These infants are already often in a state of poor nutrition which can be compounded by the problem of the diet transition. In extreme cases the difficulties can be severe enough to require hospitalization along with i.v. or i.g. diet supplementation. Thus, for a number of medical reasons ranging from allergic reactions to cows milk to metabolic disorders, many infants must be switched from their parents' original formula choice to a formula that addresses the infants special needs (e.g., soy-based formula for infants allergic to cow's milk). Very early (within the first one to four weeks) this change may present little difficulty to the infant and the caregiver. However, after about six weeks a change in the infants' diet can result in a significant amount of stress to the infant who may resist this change and produce profound anxiety in the caregiver attempting to implement the change.

Basic Research on Early Appetitive Learning. The application of the present invention to infant feeding problems is based on two fundamental phenomena. The first is the phenomenon of "conditioned appetite". Wiengarten (1984) and others have provided an important demonstration in adult animals that stimuli or signals paired with feeding can themselves come to induce ingestion. The effect is powerful enough that it will induce feeding even in animals that are sated (Weingarten, 1984). Although we have been aware since Pavlov that conditional stimuli (CS's) can cause a hungry animal to anticipate feeding (i.e., bell→salivation), conditioned appetitive CS's go beyond anticipatory conditioning in controlling ingestive behavior itself, inducing eating and influencing diet preference. The present application makes use of the possibility of conditioning appetites to an odor CS in infants and using this CS to transfer ingestion to another diet.

The second basis for the present invention method is the revelation over the last 15 years that infant mammals, including humans, are capable of remarkable appetitive learning (see reviews by Hall & Oppenheim, 1981; Spear & Rudy, 1991). In retrospect, it may seem somewhat surprising, but before the recent era of learning-development studies in animals and human infants, newborns were, with a few exceptions, viewed as deficient in learning capabilities, only showing learning to a very limited degree, and only when strong aversive stimuli were used. However, beginning in the early 1980s, studies in neonatal rodents and humans have shown that infants are capable of impressive and often complex learning and conditioning, and that such learning is likely to play a role in their ongoing behavior and to continue to influence their behavior throughout life.

Experiments in developing rodents are particularly relevant to our proposed diet-transition technique. In 1979, Johanson & Hall showed that one-day-old rat pups would learn to probe into soft paddles over their heads in order to receive milk infusions into their mouths. Most importantly, they would learn to distinguish between two paddles (one providing a milk infusion, the other not) on the basis of an odor on the paddle; the odor itself comes to evoke an appetitive response. Thus, infant rodents born in an even less developed stage than humans, are capable of odor-based appetitive learning from the time of birth. This study and others like it provoked a flurry of investigations of learning in very young mammals over the last 15 years. Such studies culminated in work showing learning as early as late fetal stages in rodents and humans (Fifer, 1987; Stickrod, Kimble, & Smotherman, 1982) and have established beyond doubt the remarkable learning capabilities of neonates.

From the point of view of the present application, the most relevant prior art is a series of studies in developing rodents showing conditioned appetites from very early ages using olfactory stimuli. When odor conditioned stimulus (CS)'s are pared with milk infusions into the mouths of rat pups, pups develop conditioned preferences for the odors (Johanson & Hall, 1982) and also develop conditioned mouthing responses (Johanson, Hall, & Polefrone, 1984). The learning is robust. It occurs with relatively few pairings (5 to 15) and is long lasting (<one week). It is also specific to the odor CS that is used. Most importantly, in infant rodents, conditioned odor CS have been shown to be capable of influencing ingestion of non-referred solutions in a paradigm parallel to the application we are describing here (Johanson & Terry, 1984). Thus, odor conditioning in infant mammals can work to influence appetitive behavior and ingestion.

Note that that odors work well as stimuli in these studies because they are particularly appropriate signals for conditioning in infants. Olfaction is one of the sensory dimensions to which infant mammals are most attuned because of its role in suckling. The olfactory system is operable very early (Alberts, 1984) and has been shown to be important in guiding suckling behavior in numerous species including rats (Feicher & Blass, 1997), cats (Rosenblatt, 1971), and humans (Schaal, 1988). Odors are also naturally and readily linked with the act of ingestion (Rozin, 1982). Thus, they provide particularly good cues for use in influencing diet transitions. The present invention teaches an applied method of managing olfactory stimuli in the suckling situation.

Studies in Human Infants Showing Presence of Relevant Mechanisms. For human infants, there are no comparable studies on a direct influence of olfactory conditioning on feeding. However, it is expected that the appetitive conditioning phenomenon is likely to generalize to other mammals including humans. Below are listed other factors which indicate that the present invention can improve human diet transitions.

First, we can be sure that taste and olfactory responsiveness are comparably well developed in rodents and humans. As has been shown in the compelling photographic documentation and analysis of Steiner (1977), from the day of birth, newborn humans are quite expressive with regard to their early appreciation of sweet and bitter tastes (also Desor, 1973). Responsiveness to odors is well developed in infants as well. Infants have been observed to respond to a range of artificial food odors prior to their first feeding (Steiner, 1977; also Engin, Lipsitt, & Kaye, 1963). Of particular relevance is the demonstration that infants may have intrinsic differential responsiveness to olfactory stimuli, with some stimuli being more preferred than others (Makin & Porter, 1989; Porter, Makin, Davis, Christensen, 1991).

Second, studies of learning and conditioning in human neonates have confirmed that the same general mammalian capabilities exist as described for other mammals above. In one of the early demonstrations before the modern era, Marquis (1931) demonstrated that sucking responses were capable of being conditioned by pairing a buzzer with the presentation of the infant's bottle. Instrumental conditioning of sucking has also been demonstrated (e.g. Kron, 1968). A good example of more recent work is that of Blass, Ganchrow, and Steiner (1984) showing that in newborn babies a small amount of sucrose squirted into the mouth will induce appetitive responses that can be conditioned to a tactile stimulation of the forehead. Blass's studies have also demonstrated a parallel neurobiological substrate for the reinforcement mechanisms in human and rodent infants (Blass, 1990), providing a further generalization across species.

Third, it is known that odors work well as learning signals in human infants. Infants who received odor stimuli paired with a form of gentle stroking showed head-turning and preference for the odor on the next day (Sullivan et al., 1991). The preferences were specific for the odor that received the conditioning. Conditioned preference was true for infants that were in a variety of behavioral states at the time of training and testing. More generally, infants are quick to learn about the olfactory characteristics of stimuli in their world and recognize the odors of their parents (feeders) with little experience (Porter, et al., 1991). Thus, while there are no specific demonstrations of conditioned olfactory modulation of ingestion in humans, there is ample indication that such conditioning is likely to work, as it does in animals.

We should point out that for human babies, introducing additional olfactory stimuli in the feeding situation should not be viewed as creating an unnatural form of stimulation or experience. During normal breast feeding, infants experience a range of olfactory stimulation or experience including olfactory stimulation from the mother's skin. In addition, breast milk contains the odors of foods the mother has recently ingested (Mennella & Beauchamp, 1994; Mennella, 1995). Breast-feeding thus provides a rich array of olfactory experience and variation in diet flavor. By contrast, formula-feeding can be viewed as a relatively monotonous flavor alternative for infants; an unnaturally impoverished one.

The present invention teaches the placement of an absorbent dot on a feeding container at a location which will place the dot near the user's nasal passages during feeding. The dot is filled with an odorant before feeding.

SUMMARY OF THE INVENTION

The main aspect of the present invention is to provide an absorbent dot on a feeding container.

Another aspect of the present invention is to add a chosen odorant to the dot to induce ingestion of food in the container.

Another aspect of the present invention is to condition a positive value to the odorant dot by pairing it with the ingestion of a first food, then by using this conditioned odorant dot to induce the acceptance of a new diet by switching it to the new diet.

Other aspects of this invention will appear from the following description and appended claims, reference being made to the accompanying drawings forming a part of this specification wherein like reference characters designate corresponding parts in the several views.

The present invention addresses the problem of diet transitions in suckling infants. The device, which is referred to as a "flavor-dot", aids diet transitions in suckling infants. The flavor-dot makes use of principles from learning and conditioning research and is derived from basic animal research studies of learning and feeding development. Flavor-dots provide a simple and convenient way to provide odor stimuli while infants suck normally from their bottle. With these devices, olfactory conditioning training can be carried out using an infant's regular formula. After a short period of training, during which positive responses to the odor become trained or conditioned, flavor-dots can be used to induce or assist the ingestion of a new diet by placing the flavor-dot on the bottle containing the new formula.

Preliminary studies confirm the intake-enhancing potency of flavor-dots and demonstrate the potential utility of the product. This device can greatly enhance the ease of transition of infants to new diets or allow the temporary introduction of therapeutic fluids. As such, it will be useful to parents whose infants are changing diets, whether these changes are only modest transitions due to convenience factors or temporary illness or more difficult changes related to medical need. In such latter cases, the use of flavor-dots can reduce the disruption of development caused by poor nutrition by facilitating the introduction of the necessary supplements, and reduce the cost and duration of treatment.

BRIEF DESCRIPTION OF THE DRAWINGS

FIG. 2 is a table showing a schedule of experiments.

FIG. 4 is a bar chart showing the mean intake of water.

FIG. 5 is a table showing the initial exposure.

FIG. 6 is a graph showing the effect of repeated tests.

Before explaining the disclosed embodiment of the present invention in detail, it is to be understood that the invention is not limited in its application to the details of the particular arrangement shown, since the invention is capable of other embodiments. Also, the terminology used herein is for the purpose of description and not of limitation.

DESCRIPTION OF THE PREFERRED EMBODIMENT

Figure 10:
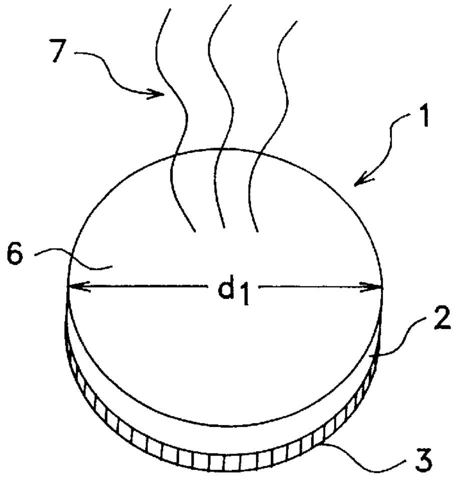
FIG. 10 is a top perspective view of a flavor-dot.

Referring first to FIG. 10 a preferred embodiment of the flavor dot 1 is made of a body 2 and an adhesive layer 3. Adhesive layer 3 is made of a non-toxic glue that is removable so the flavor dot 1 can be replaced. Preferably the glue is waterproof. However, another embodiment for easier removal provides a water based glue having a water resistant layer (not shown) between the glue and the absorbent pad. Diameter $d_1$ nominally equals 60 mm.

The body 2 must be made of an absorbent material such as cotton, felt, paper, blotter paper and filter paper. The body 2 is impregnated with an odorant 6 which emits an odor when wet. Preferably the odorant 6 can be applied to the body in any fashion: soaking, spraying, ground and glued, etc. Preferably a liquid containing the odorant dries into the absorbent material. The solvent has been alcohol or water, but is not important as long as it disappears and the residue of odorant is soluble in water. Preferably commercially available vanilla and strawberry odorants are used. The commercially available "scratch and sniff" technique could also be used, but it is not as effective as it does not last as long.

The best odorant to date is vanilla. The criteria are that the odorant is non toxic and unlikely to cause allergic reactions. The commercially available natural or artificial strawberry odors that were tested from the supermarket were all different. The exact formulas are all proprietary. Thus, any commercially available odorant that the baby likes will suffice.

Figure 11:
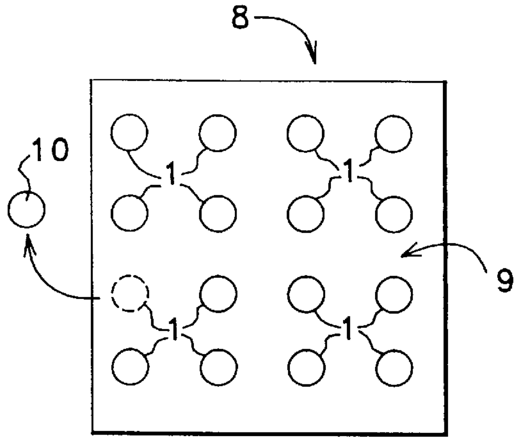
FIG. 11 is a top perspective view of a sheet of flavor-dots.

Referring next to FIG. 11 the preferred embodiment of the packaged flavor-dot 1 is shown as a multi-dot sheet 8 having a plurality of flavor-dots 1. The sheet 9 is preferably made of wax paper. In operation, the user peels off a flavor-dot 10, sticks it to a baby bottle as shown in FIG. 1, and activates the odorant 6 by touching the flavor-dot 1 with a wet fingertip.

Figure 1:
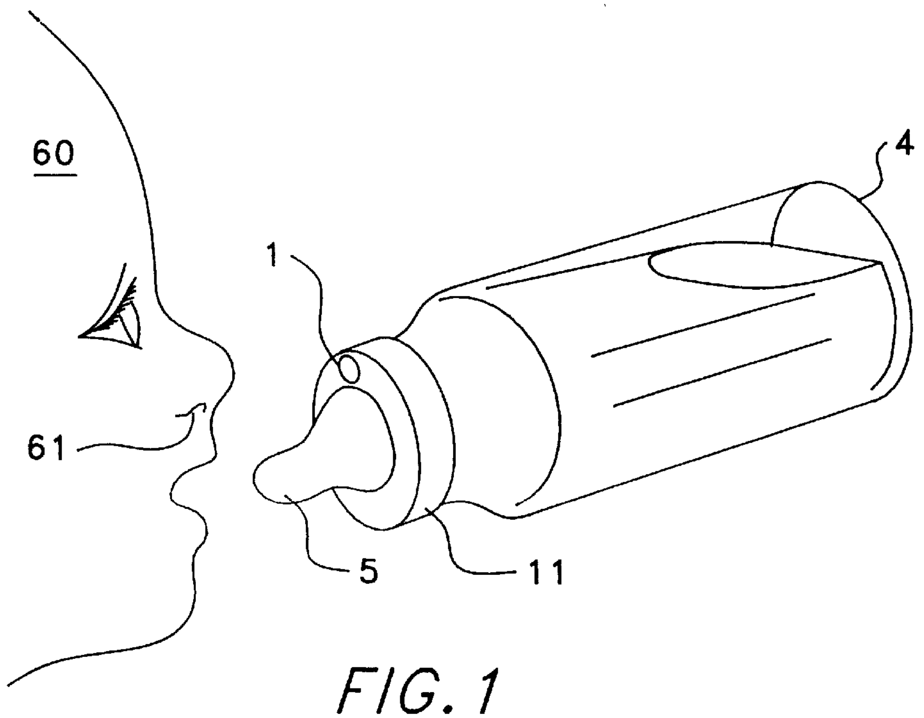
FIG. 1 is a perspective view of a baby using a flavor-dot on a bottle.

In FIG. 1 the infant 60 is presented with the odor 7 as the bottle 4 is brought to the mouth. The infant 60 continues to experience the odor during the sucking of the bottle. The caretaker is asked to make certain that the flavor dot 1 stays positioned under the infant's nostrils 61. The odors 7 are mild and usually not apparent to the person feeding the infant.

Figure 17:
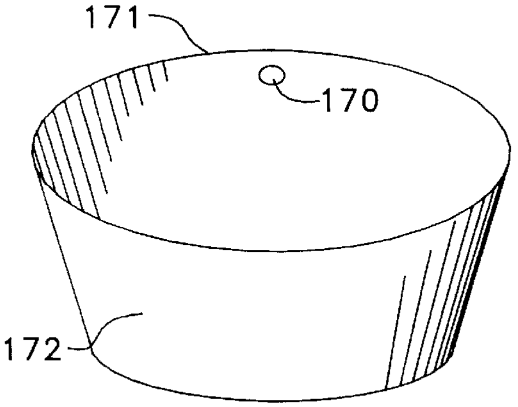
FIG. 17 is a perspective view of a bowl having a flavor dot.

FIG. 17 shows an equivalent embodiment wherein a bowl 172 has a flavor dot 170 placed along an upper inside periphery 171. It is know that equivalents to the bowl include cups, glasses and plate rims. Babies, elderly people and even pets can use these embodiments.

Figure 12:
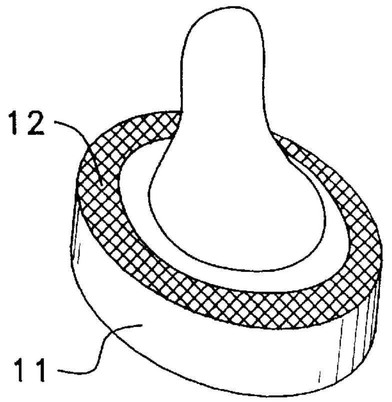
FIG. 12 is a top perspective view of a flavor-ring alternate embodiment.
Figure 18:
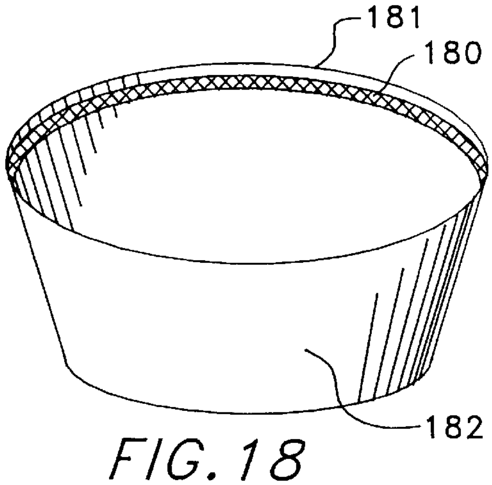
FIG. 18 is a perspective view of a bowl having a flavor ring.

In an alternate embodiment shown in FIG. 12 a flavor-ring 12 is shown affixed to the cap 11. This allows the infant to keep the odor in his nostrils without a caretaker's assistance. The ring could be made of felt. FIG. 18 shows an equivalent bowl 182 having a flavor ring 180 near the upper inside periphery 181.

Figure 13:
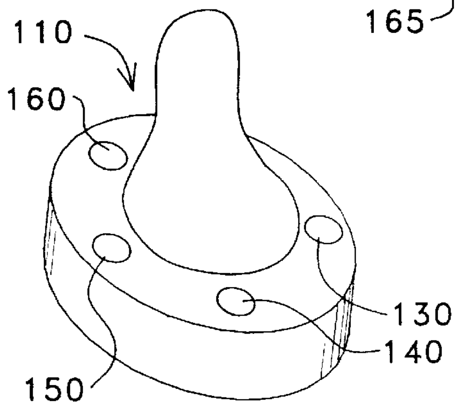
FIG. 13 is a top perspective view of a multi-dot alternate embodiment.
Figure 19:
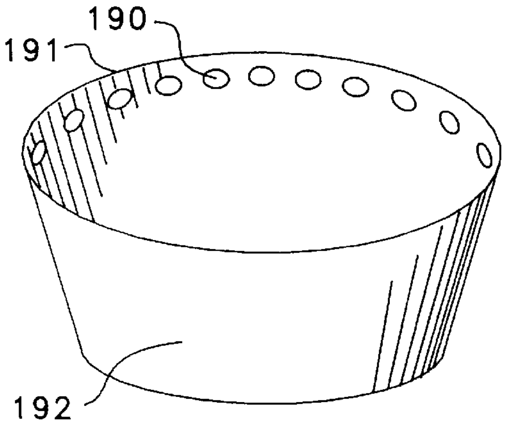
FIG. 19 is a perspective view of a bowl having a plurality of flavor dots.

Referring next to FIG. 13 a multi-dot nipple retaining ring 110 is shown. Flavor dots 130, 140, 150, 160 each contain an odorant. Each odorant could be different to provide a "menu" of olfactory experiences for the user. FIG. 19 shows an equivalent bowl 192 having a plurality of flavor dots 190 places along the upper inside periphery 191.

Figure 14:
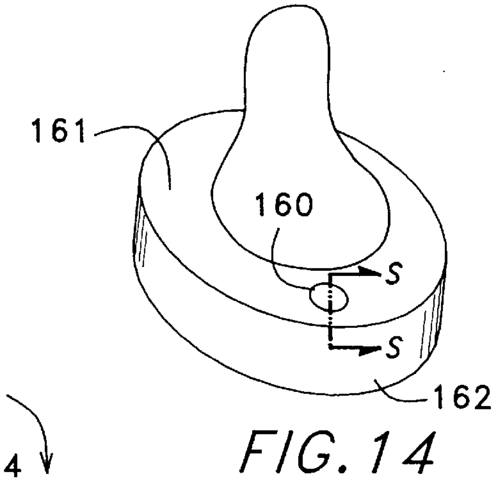
FIG. 14 is a top perspective view of a scratch and sniff alternate embodiment.

Referring next to FIG. 14 a scratch and sniff flavor dot 160 is shown located on the upper surface 161 of the nipple retaining ring 162. When the outer emulsion layer 163 is scratched off, then the odorant is released into the air.

Figure 15:
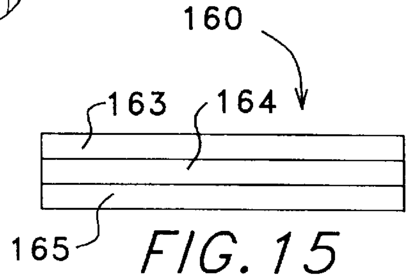
FIG. 15 is a cross sectional view of the scratch and sniff embodiment of FIG. 14.

A paper or equivalent backing layer 164 is known in the art. The adhesive layer 165 as shown in FIG. 15 is required to adhere the flavor dot 160 to a nipple retaining ring 162.

Figure 16:
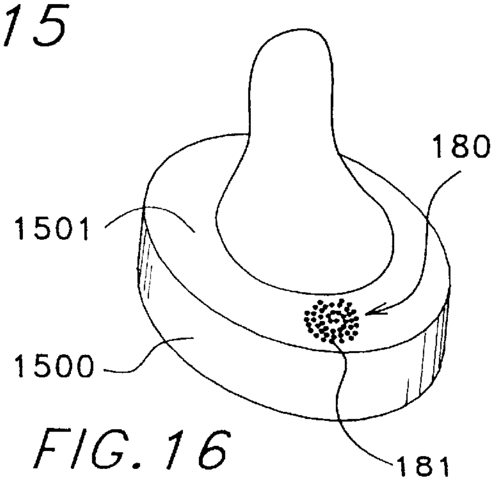
FIG. 16 is a top perspective view of an alternate embodiment having a nipple retaining ring containing a plurality of holes which hold an odorant.
Figure 20:
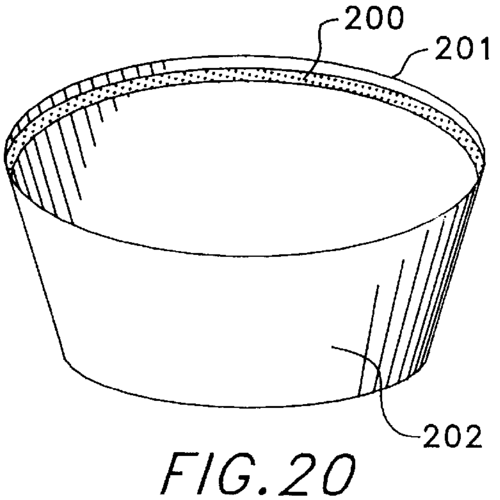
FIG. 20 is a perspective view of a bowl having a plurality of holes along a upper inside periphery, said holes having an odorant.

Referring next to FIG. 16 a nipple retaining ring 1500 has an upper surface 1501. Small holes 180 contain an odorant 181 which when wetted releases its odor. FIG. 20 shows an equivalent bowl 202 having a ring of small holes 200 along the upper inside periphery 201.

Another possible use of the present invention would be to provide an enriched olfactory environment for babies or others, much like the equivalent of a mobile for visual enrichment. In theory, such stimulation would stimulate development by increasing overall ingestion. If the odors were of future foodstuffs, then the odors and conditioning thereto would make later transfer easier.

Test Results

Testing the Product's Potential. The potential of the flavor-dot method to ease diet transitions in suckling infants was evaluated. It was found that flavor-dots could impressively enhance the ingestion of a test solution that was previously non-preferred. It is believed that this effect can be used to influence ingestion in real-world settings. Thus, as a commercial product, this device has the potential to: enhance the transitions of infants to new diets; reduce the disruptions of development caused by some feeding problems; facilitate the duration of treatment. The potential effectiveness of flavor-dots was tested in two ways: 1) whether the pairing of an olfactory stimulus with an infants consumption of normal formula using the flavor-dot method would subsequently result in increased sucking of a novel or non-preferred solution (water) in the presence of the same flavor-dot odor; and 2) evaluation of duration of the flavor-dot conditioning effect in enhancing acceptance of a novel or non-preferred solution over a period of days.

Because we focused testing was on whether training with flavor-dots could enhance intake, the experimental design was straightforward (see FIG. 2). On our first day with an infant (day 1), we recorded two minute sucking and intake baselines for the novel test solution (water), the infant's standard formula, and then the standard formula with a flavor-dot placed on the bottle (cf., FIG. 1).

Following these baseline measures the caregiver was instructed to place a flavor-dot on the bottle for every formula feeding (days 1–3) until the experimenter returned three days later (day 4). Overall, parents were diligent in following our instructions. Over the 18 infants reported here, there were only 3 missed flavor-dot bottles. This is especially encouraging as the parents were using the flavor-dots method only for research purposes, not in its proposed use of benefiting a diet transition in their own children. On our second visit (day 4) we again recorded sucks and intake during three two-minute tests (see FIG. 2). During these three tests, the infant was given a bottle with water (novel liquid) with each of three different "dots", counterbalanced across infants for order. This resulted in six different orders of testing that were the basis for subsequent analysis. In addition, two different scented flavor-dots served as flavor A and B; for two thirds of the subjects the "trained" flavor-dot (A) was a vanilla scent and the novel or "untrained" flavor-dot (B) was an imitation strawberry scent. This was reversed for the remaining third of the subjects. A third flavor-dot (C) was always unscented or "plain". It is noteworthy that of all the infants who began testing, 100% completed. There were no complications and no lack of ability to comply with the procedure.

Figure 3:
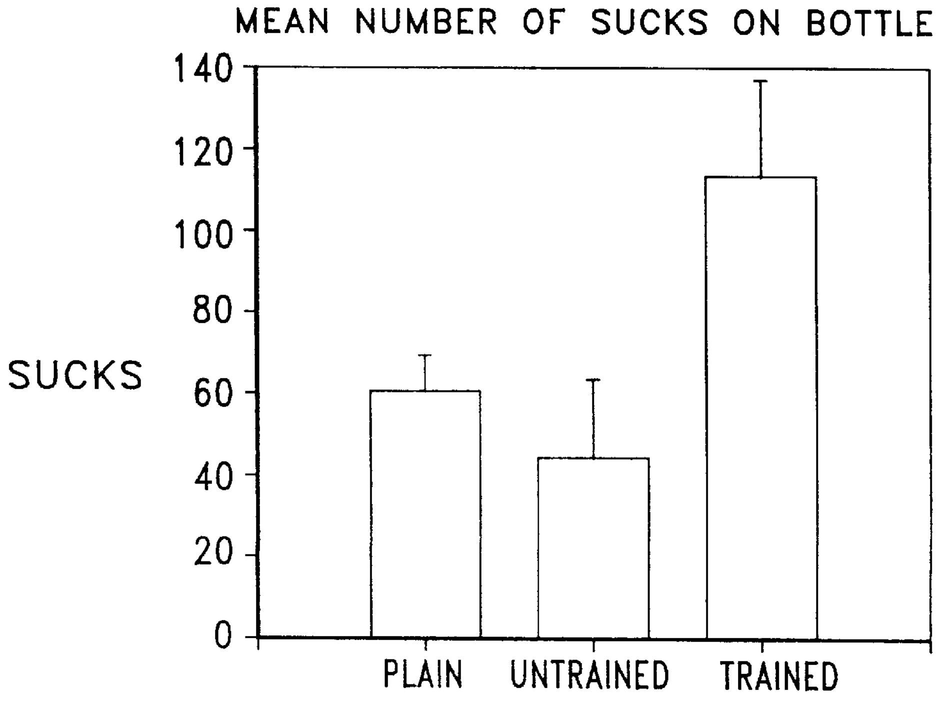
FIG. 3 is a bar chart showing the mean number of sucks on bottle.

Flavor-dot's Influence on Suckling. In brief, flavor-dots greatly increased the acceptance of a novel liquid. Infants that were tested with the trained flavor-dot on the bottle sucked more (FIG. 3) and consumed more water (FIG. 4) during the first two-minute observation than infants tested with either the plain or untrained flavor-dot. The critical real-world comparison here is between infants tested first with the flavor-dot effect and those tested with the plain bottle. In our experimental design, this corresponds to a comparison of the six infants who had the trained flavor-dot first to the six that had the plain flavor-dot. The flavor-dot effect on intake in this comparison is strong enough to be significant even with only six infants per group [$t(10)=2.26$,; $p<0.05$]. Indeed, flavor-dot training increased intake of water to almost the level of formula intake in the 2 minute test (from 50% at the initial baseline level to 91% with the flavor-dot present).

Importantly, flavor-dots increased intake because of pairing with formula (i.e. conditioned intake) rather than simply make infants respond more because of a novel odor on their bottle. When infants were tested with a novel odor (untrained flavor-dot) on the bottle they actually decreased the number of sucks on the bottle or their intake of water. This means the training effect was specific to the odor trained. Infants did not confuse or generalize between the two odors. That is, all infants had experience with an odor during the three training days and it was only the odor they were trained with that served to increase responding on the test day.

A More Detailed Consideration of the Flavor-Dot Effect. Now considering the results in more detail and in terms of the overall experimental design: Eighteen subjects were tested during our experiment. Five males and thirteen females participated in the study. Three infants (about 17% of the subjects) were African-American, the remaining fifteen (83%) were Caucasian. Subjects were initially recruited by a letter introducing Appetek, Inc., and the nature of the research to be conducted. Names and addresses were from the Wake County Birth Records obtained from the county. This list is mailed by Wake County to interested parties monthly. Each introductory letter contained a stamped response card that interested parents returned to Appetek. Subjects were then telephoned to confirm their interest and screen out subjects that did not meet our criteria regarding age, the number of diets (formulas) the child has experienced, willingness to use a novel liquid, and general health. If potential subjects met all the criteria, then we scheduled the three visits to the home.

We saw no difference in either the initial reactions to the two different odors we employed as the training stimuli (vanilla and strawberry) or in their effectiveness. Because of this lack of difference, data were collapsed across the two flavor-dot odors used during training and testing and are hereafter simply referred to as the trained and untrained flavor-dots. We analyzed the data using a between groups measure for the three infants in each condition. That is, three infants were tested within each of the six orders of flavor-dot presentation (i.e. a 6 Between ×3 Within ANOVA).

Baseline. Before examining the effects of flavor-dots on transfer, it is important to note that flavor-dot did not influence sucking or intake upon initial exposure, which can be seen in the comparison of the formula baselines. When we compare the sucking and intake of infants feeding on their standard formula before and after the introduction of the flavor-dot we see no differences in the number of sucks or the amount of intake (see FIG. 5). This means that novel odor per se does not appreciably influence the intake of a familiar diet. Thus, it is only after pairings of the flavor-dots with familiar formula that an ingestion-enhancing property was manifest.

Flavor-dot Tests. Consider first the flavor-dot effects on sucking over the three tests, as shown in FIG. 6. We have already described the large effect of training on intake on the first test. While the main effect of training is significant [$F(2,22)=8.96$, $p<0.001$], there is also a decline in the effect of the trained flavor-dot over tests. This results in a significant interaction between the order of the test and the training condition, reflecting the large First Test effect [$F(10,22)=4.33$, $p=0.002$]. We believe this interaction represents the primary piece of statistical information about the flavor-dot effect. That is, the flavor-dot effect is largest on the first trial in the situation that would be comparable to the real-world application of our procedure. This interaction reflecting a large and reliable first-test effect was also the case in the analysis of intake [$F(10,24)=2.70$, $p=0.02$].

Figure 7:
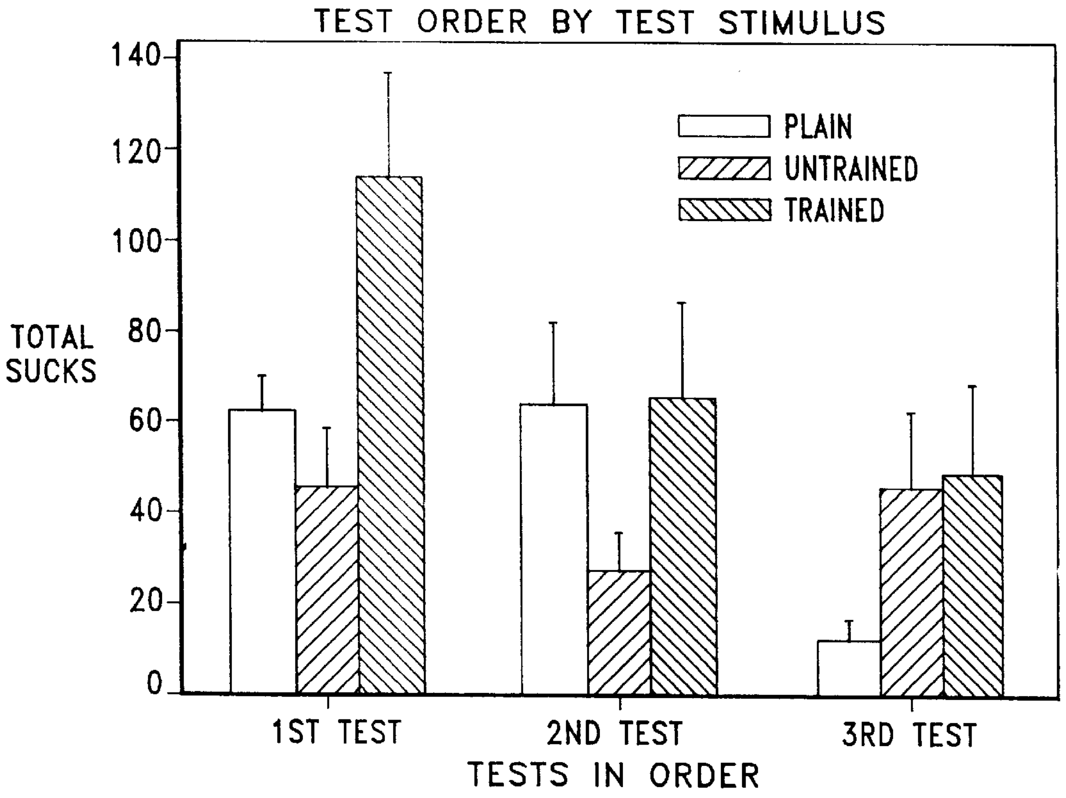
FIG. 7 is a bar chart showing the test order by test stimulus.

The decline in the effect on sucking over tests has several interesting features, and these features help place it in perspective. First, by the end of training subjects had had six minutes of ingestion of water. They were becoming increasing satiated, and this no doubt contributed to the decline in suckling over tests as seen in both the sucking and intake data as presented in FIG. 6 collapsed across training condition. A decline in sucking after three to four minutes has been reported in several studies (e.g. Nysenbaum & Smart, 1982). In retrospect, these data suggest that we should have employed shorter tests for such within-subject repeated testing. Perhaps more importantly though, because infants were all tested repeatedly, sucking on the second and third test was strongly influenced by what flavor-dot stimulus the infant had received on the first test. Both the plain and untrained value on the second test in FIG. 7 include infants that were tested with the trained flavor-dot in test 1, but the trained infants sucking on second test could have only had the plain or untrained flavor-dot on test 1. This aspect of the test design strongly works against seeing a flavor-dot training effect on the second test because infants may already be alerted to the fact that they are getting water rather than milk.

Indeed, both quantitatively and qualitatively there was a strong and telling effect of the first test odor on responding during the second test. On the second test, water with a plain flavor-dot received 98.7 (±8.2) gm if it followed an untrained flavor-dot on the first test.

Observations of qualitative responses of infants indicated that following a trained flavor-dot on the first water bottle, infants were content to accept water on the second bottle; whereas, if they had an untrained flavor-dot on the first water bottle, infants became very fussy and resistant to further test bottles. Subjectively, it was as if the use of the untrained flavor-dot had called the infants' attention to the fact that they were receiving water rather than formula, and they wanted to have nothing to do with it.

We consider these results important because they suggest that the flavor-dot training is capable of rapidly conveying an acceptability to the target solution, even if the solution is consumed in the absence of the flavor-dot. This is exactly the kind of phenomenon that is required for the flavor dot method to be useful in real diet transitions.

Figure 8:
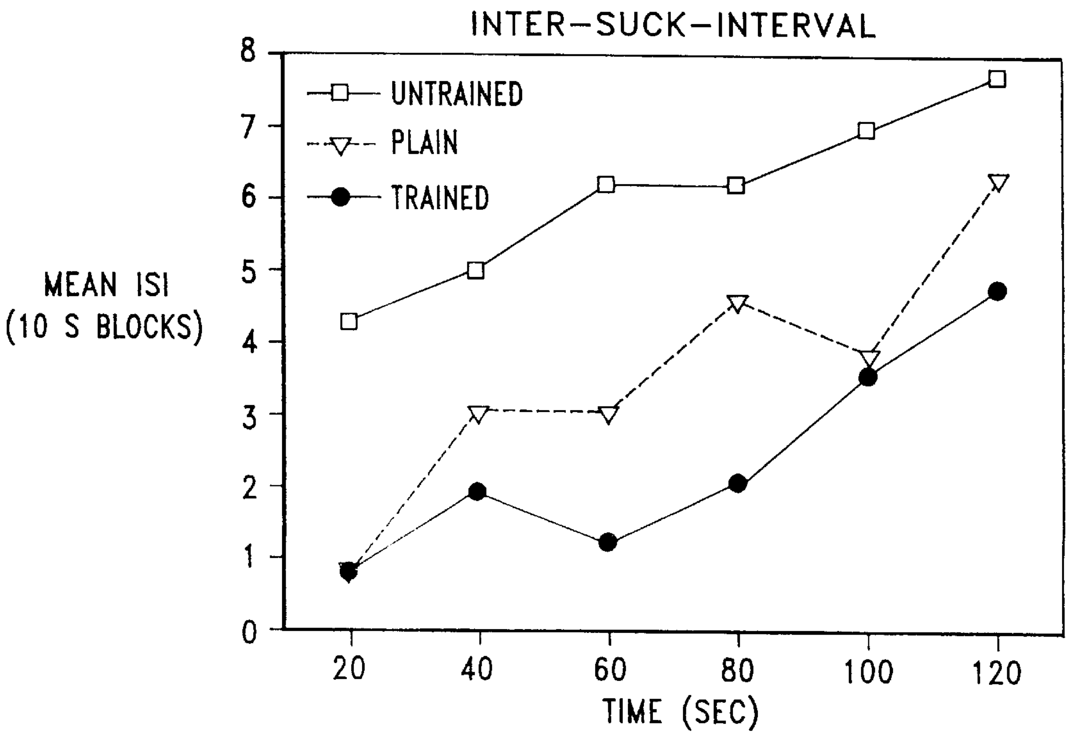
FIG. 8 is a bar chart showing the test order by test stimulus.

Sucking Rate. With our measure of sucking, it was also possible to look at the sucking rate during the testing session. To do so, we calculated the average "inter-suck-interval" (ISI; time between sucks) for each infant in 20 second time bins. FIG. 8 presents the data for each 20 seconds of the test. Shorter ISI's reflect more rapid and consistent sucking. The average ISI for sucking on standard formula is between 0.5 and 0.8 seconds compared to an ISI of about 3.5 seconds during the water baseline. FIG. 8 is a plot of the ISI for each group of six infants during their first test. Subjects tested with the trained flavor-dot had consistently shorter ISIs during the two minute test. This was particularly true during the first minute and a half or so of testing in which sucking rate was close to that for formula. (Note that because of viscosity differences, which result in flow rate differences, direct comparisons of water sucking to milk sucking can only be qualitative. In all our formal analyses, water sucking was compared to water sucking.)

Long Term Retention. A secondary aim was to evaluate the duration of the flavor-dot effect in enhancing acceptance of the novel solution. To do this we re-tested all of the infants that participated in our initial study six days after their initial test (FIG. 2—delayed test). Between the initial test of the flavor-dot and the delayed test subjects were not exposed to the flavor-dot. The delayed test was conducted exactly as the immediate test. That is, all ($r=0.86$ and $r=0.77$). That is, the infants did not change their sucking much in these control conditions. In contrast, sucking with the trained flavor-dot had a low correlation with the initial test day ($r=0.11$), reflecting the overall loss of the enhancing effect of the flavor-dot training. Interestingly and suggestively though, when considering the behavior of these infants individually, we noted that two of the six infants decreased their sucking from high levels immediately after training to practically no sucking on the delayed test six days later, while the remaining four infants continued to suck at high levels. The average sucking of these four infants was 89.5 sucks compared to 55.6 for the plain flavor-dot group and 26.7 for the untrained flavor-dot group, and they showed little overlap with these groups. Thus, some infants may be retaining the conditioning effect, while others are losing it over the retention interval.

We should point out with respect to retention that this is a relatively long interval, and it follows a test series in which infants are essentially given extinction training and no further flavor-dot training. That there was any suggestion of retention at all is impressive. In particular, we hope to take advantage of the finding that many memories may be available to infants though their strength may initially be below threshold for expression. Rovee-Collier and her colleagues (e.g. Rovee-Collier & Hayne, 1987) have demonstrated repeatedly in human infants that different reminder treatments can serve to enhance retention on tests occurring after a significant delay. This is true despite the fact that without the reminder treatment, infants show no memory for the training regime.

Figure 9:
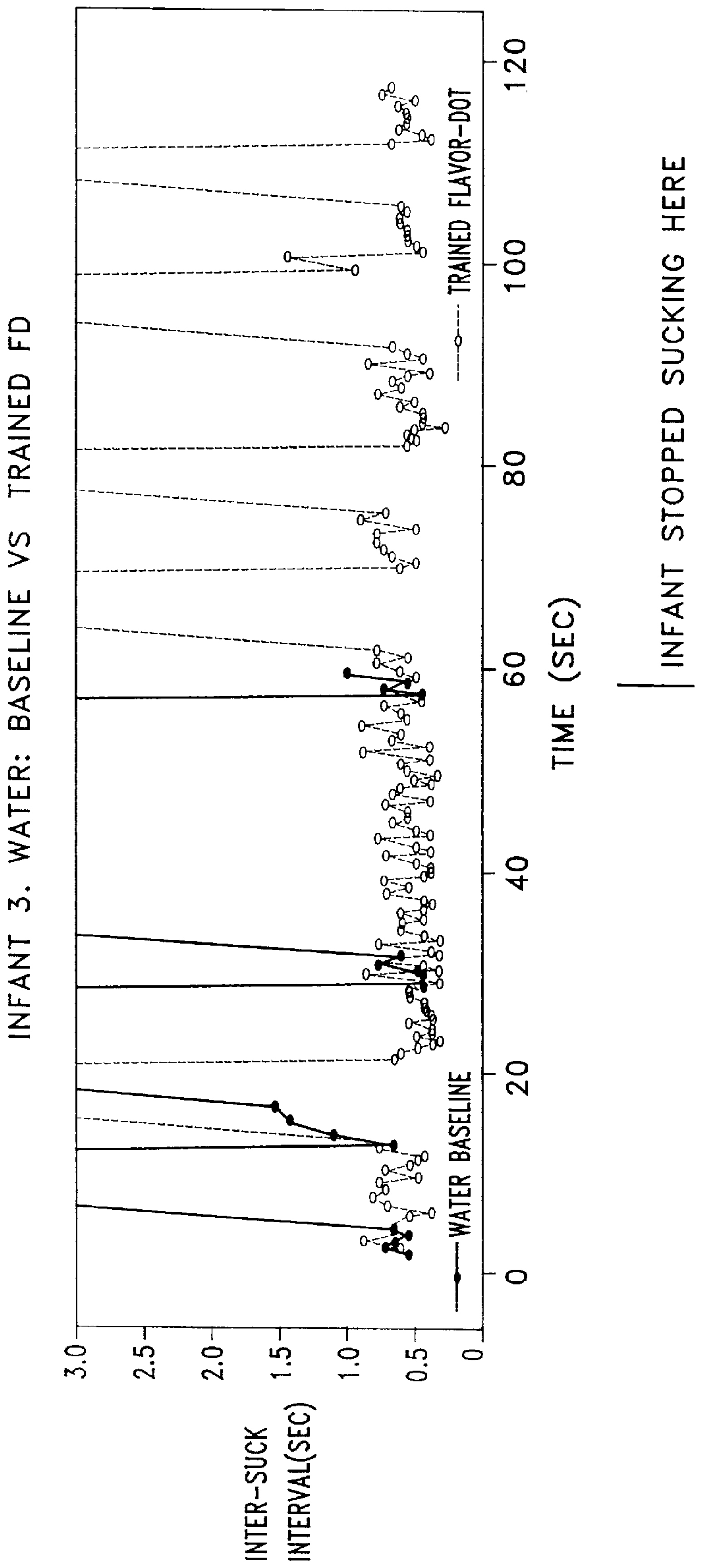
FIG. 9 is a graph showing a comparison of a water baseline and a flavor dot induced such interval.

Data from an Individual Infant. Another way to view the flavor-dot effect is in the individual sucking records. A typical record of sucks during the water baseline and the test with water with the trained flavor-dot is shown in FIG. 9. Note that during the baseline test (the filled circles), this subject sucks sporadically in three bursts during the first minute of the test and then completely fails to suck on the water bottle for the remainder of the test. Following training with flavor-dots, when this infant is re-tested with the water (the dashed line) she continues to suck throughout the two minute test with only small disruptions in her sucking. This sucking is very similar to her sucking of formula.

Anecdotes from the Field. Although the grouped data are compelling, they do not necessarily reflect how potent the flavor-dot effect can be in a given individual. For example, we observed a few cases where the flavor-dot had a remarkable effect. In one such case, a rather fussy infant (a male) was so disagreeable that he not only failed to suck or ingest much water during the baseline measure, but he also refused his formula after a short time (both before and after the flavor-dot was added) After baseline measures were complete, the flavor-dots were left with the mother to administer. On our return three days later, this particular infant, tested initially with the untrained flavor-dot, did not suck or ingest any water whatsoever. However, on the second test when the trained flavor-dot was added to the bottle, the infant quickly began to suck. In addition, these sucks seemed qualitatively different than any others we had observed previously with this infant. In this two minute period with the trained flavor-dot, the infant exceeded his total intake and sucks for all this other tests combined. After the removal of the trained flavor-dot to test the plain disk the infant returned to his previous demeanor and refused the bottle after only a single suck. Although such "all or none" responses were not universally observed in other infants, such a case is a testimonial to potential real-world potency of the flavor-dot effect.

Effectiveness Should Not Be Surprising. Despite the relatively recent experimental demonstrations of conditioning in infants, the importance of experience in shaping the development of human feeding behavior has been known and discussed since Aristotle. The phenomenon noted by Aristotle was that once infants were feeding on one diet and using one mode of feeding, it was difficult to get them to shift to another. This phenomenon represents both the problem that flavor-dots address and the conditioning process on which flavor-dots depend for efficacy.

Figure 21:
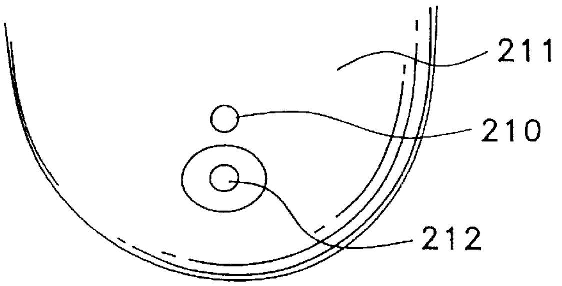
FIG. 21 is a perspective view of a human breast having a flavor dot near the nipple.

Other Applications of Flavor-dots. Flavor-dots may also prove useful as a means to generally enhance the flavor variety that bottle-fed infants experience during rearing. Variety of flavors during the suckling period may prove important to improving the range of food acceptance at weaning. It is known that breast-fed infants, who experience a natural range of flavor variety in breast milk, show a broader range of acceptance of solid foods (Sullivan & Birch, 1994). In addition, other potential uses of the device not being evaluated here might involve placing more than a single flavor-dot on the rim of the bottle so that by rotating the bottle the parent could expose the infant to a series of odors. This application of flavor-dots might prove useful in enhancing stimulation to reduce habituation to and encourage increased intake in infants who are eating poorly (i.e., flavor enhancement increases ingestion in humans in general). Flavor-dots also have a potential use in the breast-feeding to formula-feeding transition, and they may find uses in non-feeding situations (e.g. there is a form of flavored pacifier currently being test marketed). FIG. 21 shows a breast 211 having a nipple 212. The flavor dot 210 is placed near the nipple 212 to enhance ingestion. Changing the flavors can act like an equivalent to a visual mobile to generally stimulate ingestion.

Market & Marketability. The infant formula market in the United States alone is $2 billion annually (Greer & Apple, 1991). There is strong competition between the four major companies in this market. These companies are also primary providers of formula to the rest of the world. Small and questionable market ploys, such as "transitional" or "stage" diets account for shifts in sales and attest to the attentiveness of producers to any enhancements that can be made to the formula product delivery. Because of the potential utility of flavor-dots to all users of infant formula in managing minor diet transitions, in stimulating appetite, or in enhancing flavor experience, a large market exits for application of this product as most broadly conceived. While the market related specifically to difficult-diet-transition is somewhat more limited, we view this latter application as large and significant in its own right, at the same time being an application important to child health and development and one in which efficacy is specifically testable. It is, thus, a primary focus of our product evaluation.

Flavor-dots allow the convenient modification of a diet's flavor, which is largely olfactory, without needing to put additives in the diet and without altering anything the infant actually consumes. Formula companies work hard to make the flavor of formula's acceptable to infants (and their parents), but since these diet flavors must reflect a compromise, they cannot be oriented to the preferences and experiences of individual infants. The uniqueness of flavor-dots is the great flexibility they can provide in tailoring diet transition and diet enhancing manipulations to individual infants. Without the use of a selectable odor additive, this effect could only be approached by the costly alternative of having numerous versions of a diet each having different flavors. Thus, this product has a powerful potential as an accessory packaged with the infant formula, or as a point-of-sale item available in the context of a selection of formulas on store shelves.

LITERATURE CITED

Alberts, J. R., (1984). "Sensory-perceptual development in the Norway rat: A view toward comparative studies." In R. Kail & N. E. Spear (Eds.), *Comparative Perspectives on the Development of Memory* (pp. 65–101). Hillsdale, N.J.: Erlbaum.

Benson, J. D., & Masor, M. L. (1994). "Infant formula development: Past, present and future." *Endorcrine Regulations,* 28, 9–16.

Blass, E. M. (1990). "Suckling: Determinants, changes, mechanisms, and lasting impressions," *Developmental Psychology,* 26, 520–533.

Blass, E. M., Ganchrow, J. R., & Steiner, J. E. (1984). "Classical conditioning in newborn humans 2–48 hours of age." *Infant Behavior and Development,* 7, 223–235.

Cohen, J. (1988). *Statistical power analysis for the behavioral sciences.* Hillsdale, N.J.: Erlbaum.

Desor, J. A. (1973). "Taste in acceptance of sugars by human infants." *Journal of Comparative and Physiological Psychology,* 84, 496–501.

Engen, T., Lipsitt, L. P., & Kaye, H. (1963). "Olfactory responses and adaptation in the human neonate." *Journal of Comparative and Physiological Psychology,* 56, 73–77.

Fifer, W. P. (1987). "Neonatal preference for mother's voice." In N. A. Krasnegor, E. M. Blass, M. A. Hofer, & W. P. Smotherman (Eds.), *Perinatal development: A psychobiological perspective* (pp. 111–122). Orlando, Fla.: Academic Press.

Hall, W. G. & Oppenheim, R. W. "Developmental psychobiology: Prenatal, perinatal, and early postnatal aspects of behavioral development." *Ann. Rev. Psychol.,* 1987, 38, 91–128.

Hauser, H., et al. (1993). "A comparative Evaluation of whey hydrolysate and whey-predominant formulas: How well do infant accept and tolerate them?" *Clinical Pediatrics,* xx, 433–437.

Hoekelman, R. A., Friedman, S. B., Nelson, N. M., Seidel, H. M., & Weitzman, M. L. (Eds.). (1997). *Primary Pediatric Care* (Third Edition). St. Louis, Mo.: Mosby.

Johanson, I. B., & Hall, W. G. (1979). "Appetitive learning in 1-day-old rat pups." *Science,* 205, 419–421.

Johanson, I. B., & Hall, W. G. (1980). "The ontogeny of feeding in rats: III. Thermal determinants of early ingestive responding." *J. Comp. Physiol. Psychol.,* 94, 977–992.

Johanson, I. B., & Hall, W. G. (1982). "Appetitive conditioning in neonatal rats: Conditioned orientation to a novel odor." *Dev. Psychobiol.,* 15, 379–397.

Johanson, I. B., Hall, W. G., & Polefrone, J. M. (1984). "Appetitive conditioning in neonatal rats: Conditioned ingestive responding to stimuli paired with oral infusions of milk." *Dev. Psychobiol.,* 17, 357–381.

Johanson, I. B., & Terry, L. M. (1984). "Learning in infancy: A mechanism for behavioral change during development." In E. M. Blass (Ed.), *Developmental psychobiology and behavioral ecology. Handbook of behavioral neurobiology,* Vol. 9., pp. 245–281.

Kaye, H. (1967). "Infant sucking behavior and its modification." In L. P. Lipsitt & C. C. Spiker (Eds.), *Advances in child development and behavior. Vol.* 3 (pp 1–52). New York: Academic Press.

Kron, R. E. (1968). "The effect of arousal and of learning upon sucking behavior in the newborn." *Recent Advances in biological Psychiatry,* 10, 302–313.

Kron, R. E., & Litt, M. (1971). "Fluid mechanics of nutritive sucking behavior: The suckling infant's oral apparatus analyzed as a hydraulic pump." *Medical & Biological Engineering,* 9, 45–60.

Landauer, T. K. & Bjork, R. A. (1978). "Optimum rehearsal pattern and name learning." In Gruneberg, Morris, & Skykes (Eds.) *Practical aspects of memory.* New York: Academic Press.

Lipsitt, L. P., Reilly, B. M., Butcher, M. J., & Greenwood, M. M. (1976). "The stability and interrelationships of newborn sucking and heart rate." *Developmental Psychobiology,* 9, 305–310.

Makin, J. W., & Porter, R. H. (1989). "Attractiveness of lactating females' breast odors to neonates." Child Development, 60, 803–810.

Marquis, D. P. (1931). "Can conditioned responses be established in the newborn infant?" *Journal of Genet. Psychology,* 39, 479–492.

Medoff-Cooper, B., Verklan, T., & Carlson, S. (1993). "The development of sucking patterns and physiologic correlates in very-low-weight infants." *Nursing Research,* 42, 100–105.

Mennella, J. A. (1995). "Mother's milk: A medium for early flavor experiences." *Journal of Human Lactation,* 11, 39–45.

Mennella, J. A. & Beauchamp, G. K. (1994). "The infant's responses to flavored milk." *Infant Behavior and Development,* 17, 819.

Nysenbaum, A. N., & Smart, J. L. (1982). "Sucking behavior and mild intake of neonates in relation to milk fat content." *Early Human Development,* 6, 205–213.

Porter, R. H., Makin, J. W., Davis, L. B., & Christensen, K. M. (1991). "An assessment of the salient olfactory environment of formula-fed infants." *Physiology & Behavior,* 50, 907–911.

Rosenblatt, J. S. (1971). "Sucking and home orientation in the kitten: A comparative developmental study." In E. Tobach, L. R. Arnonson & E. Shaw (Eds.), *The Biopsychology of Development* (345–410). New York: Academic Press.

Rovee-Collier, C. & Hayne, H. (1987). "Reactivation of infant memory: Implications for cognitive development." In H. W. Reese (Ed.), *Advances in child development and behavior.* (Vol. 20) (pp. 185–238). San Diego, Calif.: Academic Press, Inc.

Rozin, P. (1982). "Taste-smell confusions" and the duality of the olfactory sense." *Perception & Psychophysics,* 31, 397–401.

Rubin, D. C. & Wenzel, A. E. (1996). "One hundred years of forgetting: A quantitative description of retention." *Psychological Review,* 103, 734–760.

Sampson, H. A., James, J. M., & Bernhisel-Broadbent, J. (1992). "Safety of an amino acid-derived infant formula in children allergic to cow milk." *Pediatrics,* 90, 463–465.

Santosham, M., et al. (1982). "Oral rehydration therapy of infantile diarrhea: A controlled study of well-nourished children hospitalized in the United States and Panama." *The New England Journal of Medicine,* 306, 1070–1076.

Schaal, B. (1988). Review: "Olfaction in infants and children: developmental and functional perspectives." *Chemical Senses,* 13, 145–190.

Schleidt, M., & Genzel, C. (1990). "The significance of mother's perfume for infants in the first weeks of their life." *Ethology & Sociobiology,* 11, 145–154.

Spear, N. E. & Rudy, J. W. (1991). "Tests of the ontogeny of learning and memory: Issues, methods, and results." In H. N. Shair, G. A. Barr, & M. A. Hofer (Eds.), *Developmental Psychobiology: New methods and changing concepts* (pp. 84–113). Oxford University Press: New York.

Steiner, J. E. (1977). "Facial expressions of the neonate infant indicating the hedonics of food-related chemical stimuli." In J. M. Weiffenbach (Ed.), *Taste and development. The genesis of sweet preference* (pp. 173–188). Bethesda, Md.: DHEW.

Stickrod, G., Kimble, D. P., & Smotherman, W. P. (1982). "In utero taste/odor aversion conditioning in the rat." *Physiology & Behavior,* 28, 5–7.

Sullivan, S. A., & Birch, L. L. (1994). "Infant dietary experience and acceptance of solid foods." *Pediatrics,* 93, 271–277.

Sullivan, R. M., Taborsky-Barba, S., Mendoza, R., Itano, A., Leon, M., Cotman, C. W., Payne, T. F., & Lott, I. (1991). "Olfactory classical conditioning in neonates." *Pediatrics,* 87, 511–518.

Teicher, M. H. & Blass, E. M. (1977). "First suckling response of the newborn albino rat: The roles of olfaction and amniotic fluid." *Science,* 198, 635–636.

Weingarten, H. P. (1984). "Meal initiation controlled by learned cues: Basic behavioral properties." *Appetite,* 5, 147–158.

Although the present invention has been described with reference to preferred embodiments, numerous modifications and variations can be made and still the result will come within the scope of the invention. No limitation with respect to the specific embodiments disclosed herein is intended or should be inferred.

I claim:

1. A method to increase a user's intake of a novel diet comprising the steps of:

pairing a novel odorant with a user's preferred diet;

adding the novel odorant to a container at a location which is near the user's nose during ingestion;

thereby increasing an intake of the novel diet on the basis of a classically conditioned acquired property of the novel odorant which influences ingestion.

2. The method of claim 1, wherein the user's preferred food is breast milk, and the step of pairing the novel odorant with a user's preferred food is pairing the novel odorant with breast feeding.

3. A method to stimulate overall ingestion for babies comprising the steps of:

placing an odorant on a container at a location which is near a baby's nose while he ingests from the container; and activating the odorant prior to ingestion of a contents in the container.

4. The method of claim 3 further comprising the step of selecting the odorant from the group consisting of future foodstuffs.

5. The method of claim 3 further comprising the steps of:

placing a plurality of odorants on the container at locations near the baby's nose while he ingests; and moving the container during ingestion to a place a plurality of different odorants near the baby's nose during ingestion.

6. A method to stimulate an ingestion of breast milk by a baby comprising the steps of:

placing an odorant on a breast at a location which is near a baby's nose while he ingests milk from the breast; and activating the odorant.

7. A classical conditioning method to increase a user's intake of a novel diet comprising the steps of:

pairing a novel odorant with a user's preferred food:

holding the novel odorant at a location which is near the user's nose during ingestion; and activating the novel odorant prior to ingestion of a novel diet, thereby increasing an intake of the novel diet on the basis of a classically conditioned acquired property of the novel odorant which influences ingestion.

8. The method of claim 7, wherein the step of holding further comprises affixing the novel odorant to a container.

9. A bait and switch method to increase a user's intake of a novel diet comprising the steps of:

coupling a novel odorant with a user's present diet;

putting the novel odorant near the user's nose during ingestion; and switching the present diet with a novel diet while maintaining the novel odorant near the user's nose during ingestion, thereby encouraging the user to ingest the novel diet based on his learned behavior associated with the novel odorant.

10. The method of claim 9, wherein the step of putting further comprises affixing the novel odorant to a container.

11. An olfactory stimulus for ingesting comprising:

a fluid absorbent pad;

a sticky adhesive backing affixed to the pad;

a pad fixation point on a container, said pad fixation point located near a user's nose while ingesting from the container;

said fluid absorbent pad having an odorant whose odor is attractive to the user upon an activation of odorant, thereby increasing an intake of a diet when the pad is affixed at the fixation point; and wherein said activation comprises adding a wetting solution to the odorant.

12. An olfactory stimulus for ingesting comprising:

a fluid absorbent pad;

a sticky adhesive backing affixed to the pad;

a pad fixation point on a container, said pad fixation point located near a user's nose while ingesting from the container;

said fluid absorbent pad having an odorant whose odor is attractive to the user upon an activation of odorant, thereby increasing an intake of a diet when the pad is affixed at the fixation point;

wherein the pad further comprises filter paper, and the sticky adhesive backing further comprises a resistance to water; and wherein said activation comprises scratching said odorant.

13. An olfactory stimulus for ingestion comprising:

a fluid absorbent pad;

a sticky adhesive backing affixed to the pad;

a pad fixation point on a container, said pad fixation point located near a user's nose while ingesting from the container;

said fluid absorbent pad having an odorant whose odor is attractive to the user upon an activation of odorant, thereby increasing an intake of a diet when the pad is affixed at the fixation point;

wherein the pad fixation point is atop a ring which supports a baby nipple; and wherein the ring further comprises a plurality of fluid absorbent pads each containing an ordorant.

14. The stimulus of claim 1, wherein the pad further comprises filter paper, and the sticky adhesive backing further comprises a resistance to water.

15. The stimulus of claim 1, wherein the fluid absorbent pad has a diameter of about 60 mm.

16. The stimulus of claim 15, wherein the odorant is vanilla.

17. The stimulus of claim 15, wherein the odorant is strawberry.

18. An olfactory stimulus for ingesting comprising:

a nipple retaining ring suitable to mount on a container;

said ring having an upper surface which is moved near a user's nose upon an ingestion of a liquid in the container;

said ring having a plurality of small holes on the upper surface; and an odorant whose odor is attractive to the user, said odorant located inside the small holes, whereby an activation of the odorant increases an intake of a diet.

19. An olfactory stimulus for ingesting comprising:

a fluid absorbent pad;

a sticky adhesive backing affixed to the pad;

a pad fixation point on a container, said pad fixation point located near a user's nose while ingesting from the container;

said fluid absorbent pad having an odorant whose odor is attractive to the user upon an activation of odorant, thereby increasing an intake of a diet when the pad is affixed at the fixation point; and wherein the container is a bowl, and the fixation point is on an upper inside periphery of the bowl.

20. An olfactory stimulus for ingesting comprising:

a fluid absorbent pad;

a sticky adhesive backing affixed to the pad;

a pad fixation point on a container, said pad fixation point located near a user's nose while ingesting from the container;

said fluid absorbent pad having an odorant whose odor is attractive to the user upon an activation of odorant, thereby increasing an intake of a diet when the pad is affixed at the fixation point;

said olfactory stimulas further comprising a plurality of pads, and the container further comprises a bowl, and the plurality of pads are located on a plurality of pad fixation points which are located on an upper inside periphery of the bowl.

21. An olfactory stimulus for ingesting comprising:

a bowl a ring placed along an upper inside periphery of said bowl;

an odorant permeated throughout the ring, thereby increasing an intake of a diet when a user ingesting a substance from the bowl.

22. An olfactory stimulus for ingesting comprising:

a bowl;

a ring of small holes placed along an upper inside periphery of said bowl;

an ororant located inside the small holes, whereby an activation of the odorant increases a user's intake of a substance from the bowl.

* * * * *

UNITED STATES PATENT AND TRADEMARK OFFICE
CERTIFICATE OF CORRECTION

PATENT NO. : 6,112,749 Page 1 of 1
DATED : September 5, 2000
INVENTOR(S) : Warren Grimes Hall, David Charles Rubin It is certified that error appears in the above-identified patent and that said Letters Patent is hereby corrected as shown below:

Column 1,
Lines 6-10, insert the following sentence:
-- This invention was made with government support under grant number R44 HD34330 awarded by the National Institute of Health, National Institute of Child Health and Human Development. The Government has certain rights in the invention. --

Signed and Sealed this

Seventh Day of May, 2002

*Attest:*

JAMES E. ROGAN

*Attesting Officer* *Director of the United States Patent and Trademark Office*